United States Patent [19]

Gutbier

[11] Patent Number: Plant 5,492

[45] Date of Patent: Jun. 11, 1985

[54] POINSETTIA NAMED ANGELIKA

[75] Inventor: Gregor Gutbier, Linz am Rhein, Fed. Rep. of Germany

[73] Assignee: Paul Ecke, Jr., Encinitas, Calif.

[21] Appl. No.: 510,422

[22] Filed: Jul. 1, 1983

[51] Int. Cl.[3] ..... A01H 5/00

[52] U.S. Cl. ..... Plt./86

[58] Field of Search ..... Plt./86

*Primary Examiner*—Robert E. Bagwill

*Attorney, Agent, or Firm*—Charles W. Rummler

[57] ABSTRACT

A new red poinsettia cultivar particularly distinguished by its earlier blooming and at a lower temperature than the plant that it most nearly resembles, namely Poinsettia V-14, U.S. Plant Pat. No. 4,384; and by its having the unique growth and habit characteristics of the Gutbier's Family of poinsettia plants, including easy multiple branching, full bracts, and small cyathia clusters.

2 Drawing Figures

BACKGROUND OF THE NEW PLANT

This new variety of poinsettia plant originated as a mutation of one of my seedlings grown in greenhouse at Linz (Rhein), West Germany, the said seedling being identified in my records as V-17, which resulted from extensive breeding efforts carried on by me at Linz (Rhein) with the object of obtaining distinctive and better varieties of poinsettias for the commercial market. This particular sport was selected by me for propagation and trial because of its earlier blooming and at a lower growing temperature than the conditions under which the Poinsettia V-14 was being grown. I propagated this sport, by means of cuttings, through several successive generations at Linz (Rhein) and found that its novel and distinctive characteristics held true from generation to generation and appeared to be firmly fixed.

DESCRIPTION OF THE DRAWINGS

This new poinsettia cultivar is illustrated by the accompanying full color photographic drawings, the upper one of which shows a full face view of a mature bloom of this variety and the lower one of which is a side view showing a potted plant of this variety in full bloom, the colors shown being as nearly true as can be reasonably expected from conventional commercial photographic procedures.

DESCRIPTION OF THE NEW PLANT

The following is a detailed description of my new poinsettia plant as observed of greenhouse grown plants of this variety at Encinitas, Calif., the color designations being according to The R.H.S. Colour Chart published by The Royal Horticultural Society of London, England.

THE PLANT

Origin: Sport.

Parentage: A seedling of unnamed parentage which is now identified in my records as V-17.

Classification:

*Botanic.*—*Euphorbia pulcherrima.*

*Commercial.*—Greenhouse poinsettia.

Form: Shrub.

Height: Medium to short.

Growth habit:

*As a single stem.*—Upright and vigorous with many side shoots. Normally this plant requires no growth regulator since it grows between short and medium in height. Almost all upper stem nodes produce buds and side shoots under normal greenhouse conditions and in some cases, these shoots produce rudimentary flowers.

*As a branched plant.*—This variety grows upright with many side branches which develop uniformly and produce excellent bracts on all stems, providing a bushy, full appearance. If grown too warm, however, there is some tendency toward soft branches which fall down.

Growth rate: This variety grows very much like the Annette Hegg family of poinsettias in respect of temperature for growth and number of weeks for blooming after the start of bud initiation. This plant is considered to be a nine-week variety and even though it somewhat resembles the older red variety V-14, U.S. Plant Pat. No. 4,384, it blooms a few days earlier and it can be grown at lower temperatures for similar results. This plant roots very fast, similar to other poinsettias, under modern greenhouse methods. Night temperatures during October and November normally is recommended to be about 16° C. to 18° C. but a lower night temperature the last few weeks of the growing period improves the color and provides stronger stems.

Foliage: Alternate, with slightly upwardly angled petioles and in normal abundance.

*Leaf size.*—Medium, about $3\frac{1}{2}$ to $5\frac{1}{2}$ inches long and about $2\frac{1}{2}$ to 4 inches wide.

*Leaf shape.*—Most leaves are ovate with some having undulated and serrated margins. Some leaves have acuminated tips.

*Aspect.*—Upper side — Dull with veins indented. Under side — Dull with ordinary veining.

*Color.*—Upper side — Dark Green, near R.H.S. 147A. Under side — Dark Green, near and between 147B and 137C. Often the leaf color is lighter than as described because of improper greenhouse plant nutrition for this variety. Light intensity and greenhouse temperature also affect leaf color.

Retention.—The foliage lasts well kept at a low room temperature below 20° C. and with good light intensity and proper watering.

Bracts: Generally about 12 to 17 in number, in overlapping arrangement with a tight center. The shape of the bract arrangement is somewhat unbrella-like.

*Size.*—Mature bracts are about 6 inches long and about 5 inches wide.

*Shape.*—Most bracts are ovate to elliptic, generally with acuminate tips.

*Petioles.*—Short, from about $\frac{1}{4}$ inch to 1 inch long.

*Color.*—Upper side — Near and between 45A and 46B. Under side — Near 46C. When grown under improper conditions such as too high temperature or excessive light, the color of the bracts is a medium red with a tendency toward becoming a faded red.

*Ribs and veins.*—Veining on the under side of the bract is of variable light coloration.

*Rentention.*—The bracts are of medium persistence similar to those of the Eckespoint C-1 variety (U.S. Plant Pat. No. 2,923).

This new variety of poinsettia plant is particularly distinguished by its habit of blooming earlier and at a lower temperature than its nearest rival Poinsettia V-14, U.S. Plant Pat. No. 4,384, known in Europe by the name "Franzi" and in the United States by the name "Glory", and by its possession of the unique characteristics of the Gutbier's family of poinsettia plants.

I claim:

1. A new and distinct poinsettia cultivar, substantially as herein shown and described, particularly distinguished by its habit of blooming earlier and at a lower temperature than Poinsettia V-14 (U.S. Plant Pat. No. 4,384) which it most nearly resembles.

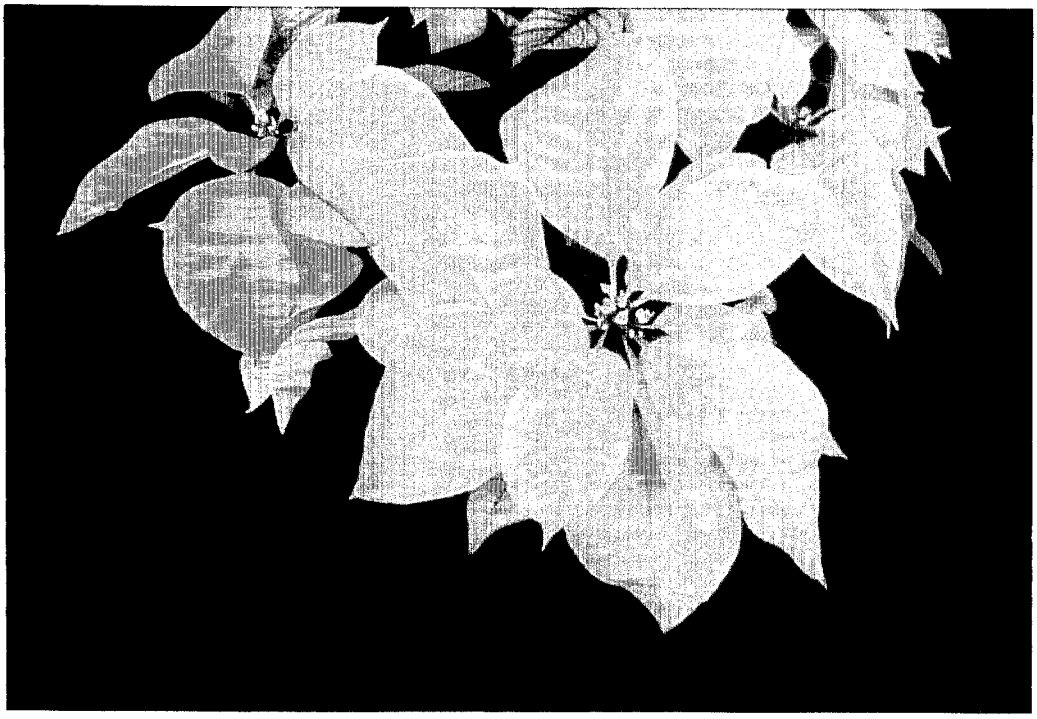
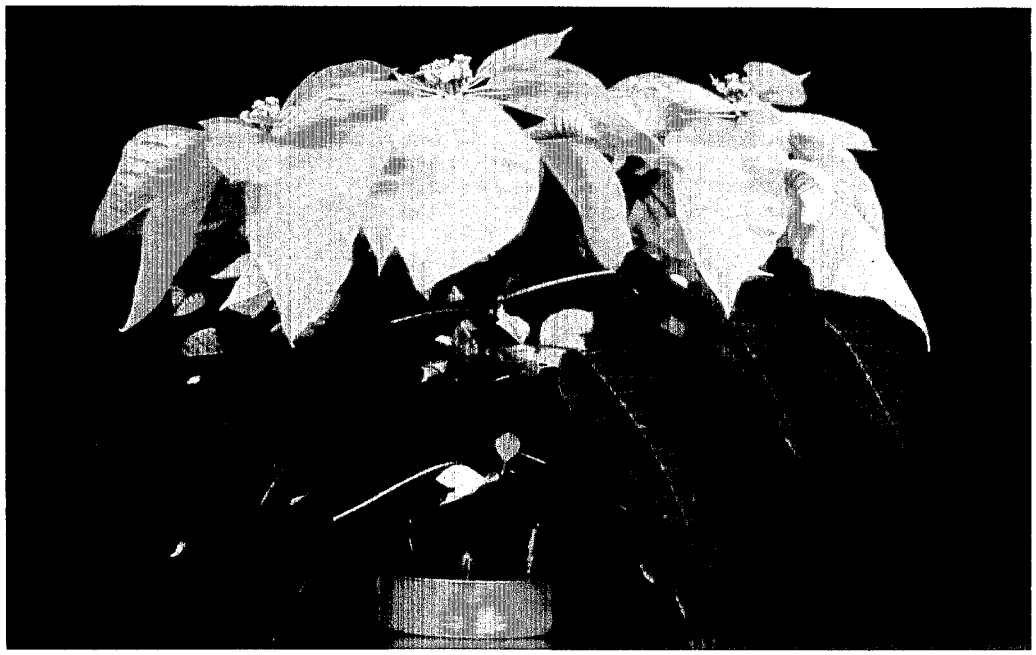

* * * * *